US010561879B2

(12) United States Patent
Huang

(10) Patent No.: US 10,561,879 B2
(45) Date of Patent: Feb. 18, 2020

(54) VIBRATION ELASTIC ROPE ASSEMBLY

(71) Applicant: AURORA SPORT TECHNOLOGY CO., LTD., Taipei (TW)

(72) Inventor: Mao-Ying Huang, Taipei (TW)

(73) Assignee: AURORA SPORT TECHNOLOGY CO., LTD., Taipei (TW)

( * ) Notice: Subject to any disclaimer, the term of this patent is extended or adjusted under 35 U.S.C. 154(b) by 111 days.

(21) Appl. No.: 15/940,437

(22) Filed: Mar. 29, 2018

(65) Prior Publication Data

US 2019/0192893 A1 Jun. 27, 2019

(30) Foreign Application Priority Data

Dec. 21, 2017 (TW) ............................. 106218965 U

(51) Int. Cl.

| | |
|---|---|
| ***A63B 21/00*** | (2006.01) |
| ***A61H 1/00*** | (2006.01) |
| ***A63B 21/055*** | (2006.01) |
| ***A63B 21/04*** | (2006.01) |
| ***A63B 21/16*** | (2006.01) |
| ***A61H 15/00*** | (2006.01) |
| ***A63B 1/00*** | (2006.01) |
| *A61B 1/00* | (2006.01) |

(52) U.S. Cl.

CPC ......... *A63B 21/00178* (2013.01); *A61H 1/00* (2013.01); *A63B 1/00* (2013.01); *A63B 21/0414* (2013.01); *A63B 21/0442* (2013.01); *A63B 21/0555* (2013.01); *A63B 21/16* (2013.01); *A63B 21/4035* (2015.10); *A61H 15/00* (2013.01); *A61H 2015/0014* (2013.01); *A61H 2201/1635* (2013.01); *A61H 2201/1695* (2013.01)

(58) Field of Classification Search

CPC ........ A63B 21/00196; A63B 21/00178; A61H 2015/0007–0021; A61H 15/00

See application file for complete search history.

(56) References Cited

U.S. PATENT DOCUMENTS

| | | | | |
|---|---|---|---|---|
| 5,681,248 | A * | 10/1997 | Vani | A63B 21/0004 482/10 |
| 9,168,411 | B2 * | 10/2015 | Holman | A63B 21/028 |
| 9,572,745 | B2 * | 2/2017 | Lin | A61H 15/0092 |
| D785,103 | S * | 4/2017 | Townsend | D21/662 |
| D794,814 | S * | 8/2017 | Higgins | D24/211 |
| 10,029,137 | B2 * | 7/2018 | Davis | A63B 21/0552 |
| 10,071,014 | B2 * | 9/2018 | Yeh | A61H 15/00 |
| 10,117,803 | B2 * | 11/2018 | Fadil | A61H 15/0092 |
| 2002/0187885 | A1 * | 12/2002 | Liao | A63B 21/0552 482/126 |
| 2004/0082447 | A1 * | 4/2004 | Chaplin | A63B 21/0004 482/124 |

(Continued)

*Primary Examiner* — Nyca T Nguyen

(74) *Attorney, Agent, or Firm* — Muncy, Geissler, Olds & Lowe, P.C.

(57) ABSTRACT

A vibration elastic rope assembly includes a vibrating unit having a cylindrical shell and a vibrator disposed in the cylindrical shell, and an elastic unit having a connecting member mounted on the cylindrical shell of the vibrating unit and an elastic rope connected to the connecting member and detachably connected to a user's body or an exercise equipment. Thus, the user can perform a stretching exercise by using the elastic unit and a vibration exercise by using the vibrating unit.

5 Claims, 6 Drawing Sheets

(56) References Cited

U.S. PATENT DOCUMENTS

| | | | | |
|---|---|---|---|---|
| 2008/0023899 | A1* | 1/2008 | Hasegawa | F16F 7/108 267/141.1 |
| 2008/0077058 | A1* | 3/2008 | Klearman | A61H 19/00 601/70 |
| 2008/0108484 | A1* | 5/2008 | Wu | A61H 15/0092 482/122 |
| 2008/0200851 | A1* | 8/2008 | Faussett | A61H 15/0092 601/119 |
| 2008/0269029 | A1* | 10/2008 | Heck | A61H 11/02 482/129 |
| 2010/0113992 | A1* | 5/2010 | Godfrey | A61H 15/0078 601/70 |
| 2011/0183825 | A1* | 7/2011 | Yang | A63B 21/4039 482/132 |
| 2011/0312477 | A1* | 12/2011 | Wiseman | A63B 21/0442 482/126 |
| 2012/0065557 | A1* | 3/2012 | Phillips | A61H 15/0092 601/99 |
| 2012/0209154 | A1* | 8/2012 | Williams, III | A61F 7/02 601/19 |
| 2014/0128786 | A1* | 5/2014 | Ross | A61H 15/0092 601/118 |
| 2014/0371639 | A1* | 12/2014 | Diecidue | A61H 15/00 601/19 |
| 2015/0090193 | A1* | 4/2015 | Giarrizzo | A01K 15/026 119/709 |
| 2015/0190304 | A1* | 7/2015 | Lawrie | A61H 15/0092 601/118 |
| 2017/0106249 | A1* | 4/2017 | Marton | A63B 43/004 |
| 2017/0274239 | A1* | 9/2017 | Barella | A63B 21/0552 |
| 2018/0055724 | A1* | 3/2018 | Slocum | A61H 23/0263 |
| 2019/0175977 | A1* | 6/2019 | Miri-Ghomizadeh | A63B 21/0557 |

* cited by examiner

VIBRATION ELASTIC ROPE ASSEMBLY

BACKGROUND OF THE INVENTION

1. Field of the Invention

The present invention relates to exercise equipment, and more particularly to a vibration elastic rope assembly.

2. Description of the Related Art

An elastic rope is a popular strength training tool. When in use, one end of the elastic rope is trampled under the user's feet or fastened to a wall, and the other end of the elastic rope is pulled and relaxed repeatedly by the user's hand, such that the user can perform the biceps or triceps exercise. However, the way of operating the conventional elastic rope is dull and boring, and furthermore, it is difficult for the user to perform different types of exercises by using the conventional elastic rope. Therefore, it is desirable to provide a vibration elastic rope assembly that eliminates the aforesaid drawbacks.

SUMMARY OF THE INVENTION

It is a primary objective of the present invention to provide a vibration elastic rope assembly, which allows a user to perform different types of exercises.

To attain the above objective, the present invention provides a vibrating unit and an elastic unit. The vibrating unit has a cylindrical shell and a vibrator disposed in the cylindrical shell. The elastic unit has at least one connecting member mounted on the cylindrical shell of the vibrating unit and an elastic rope connected to the connecting member and detachably connected to the user's body or exercise equipment, thereby enabling the user to perform different types of exercises.

In a preferred embodiment of the present invention, the elastic unit has two said connecting members. The two connecting members, which are annular belts, are sleeved on the cylindrical shell of the vibrating unit and connected to two ends of the elastic rope, respectively. Preferably, the two connecting members are spaced apart at a predetermined distance.

In another preferred embodiment of the present invention, the elastic unit has one said connecting member. The connecting member is an annular belt and sleeved on the cylindrical shell of the vibrating unit. One end of the elastic rope is connected to the connecting member, and the other end of the elastic rope is detachably connected to the user's body or the exercise equipment.

Preferably, the cylindrical shell has a plurality of flexible protrusions at an outer surface thereof to improve the user's blood circulation.

As a result, the user can step on the elastic rope and lift the vibrating unit repeatedly to train different muscle groups, and further, the vibration generated by the vibrator can be transmitted to the cylindrical shell and the elastic rope for enabling the user to perform a vibration exercise.

DETAILED DESCRIPTION OF THE INVENTION

Figure 1:
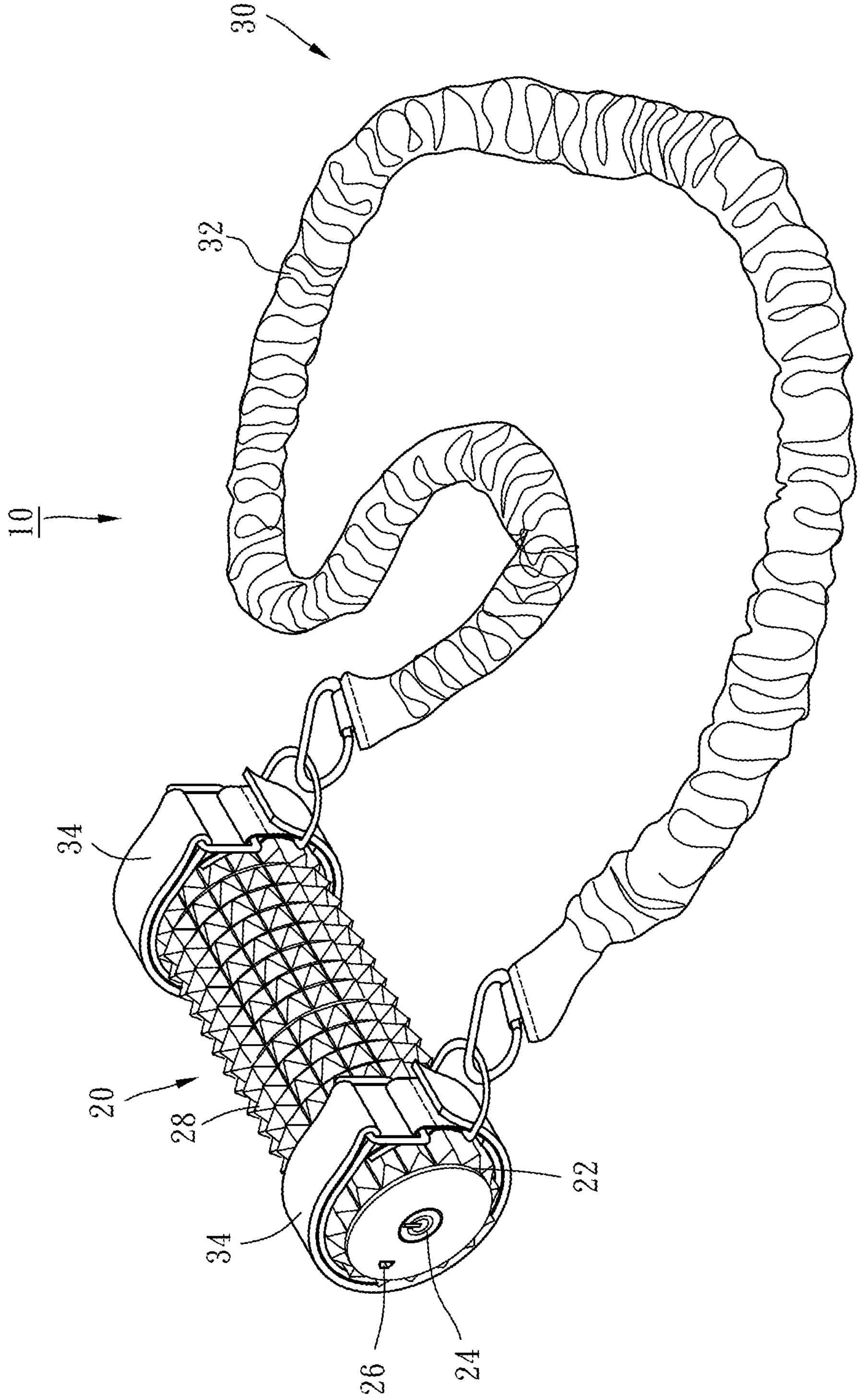
FIG. 1 is a perspective view of a vibration elastic rope assembly according to a first preferred embodiment of the present invention, showing the two connecting members are sleeved on two ends of the cylindrical shell.
Figure 2:
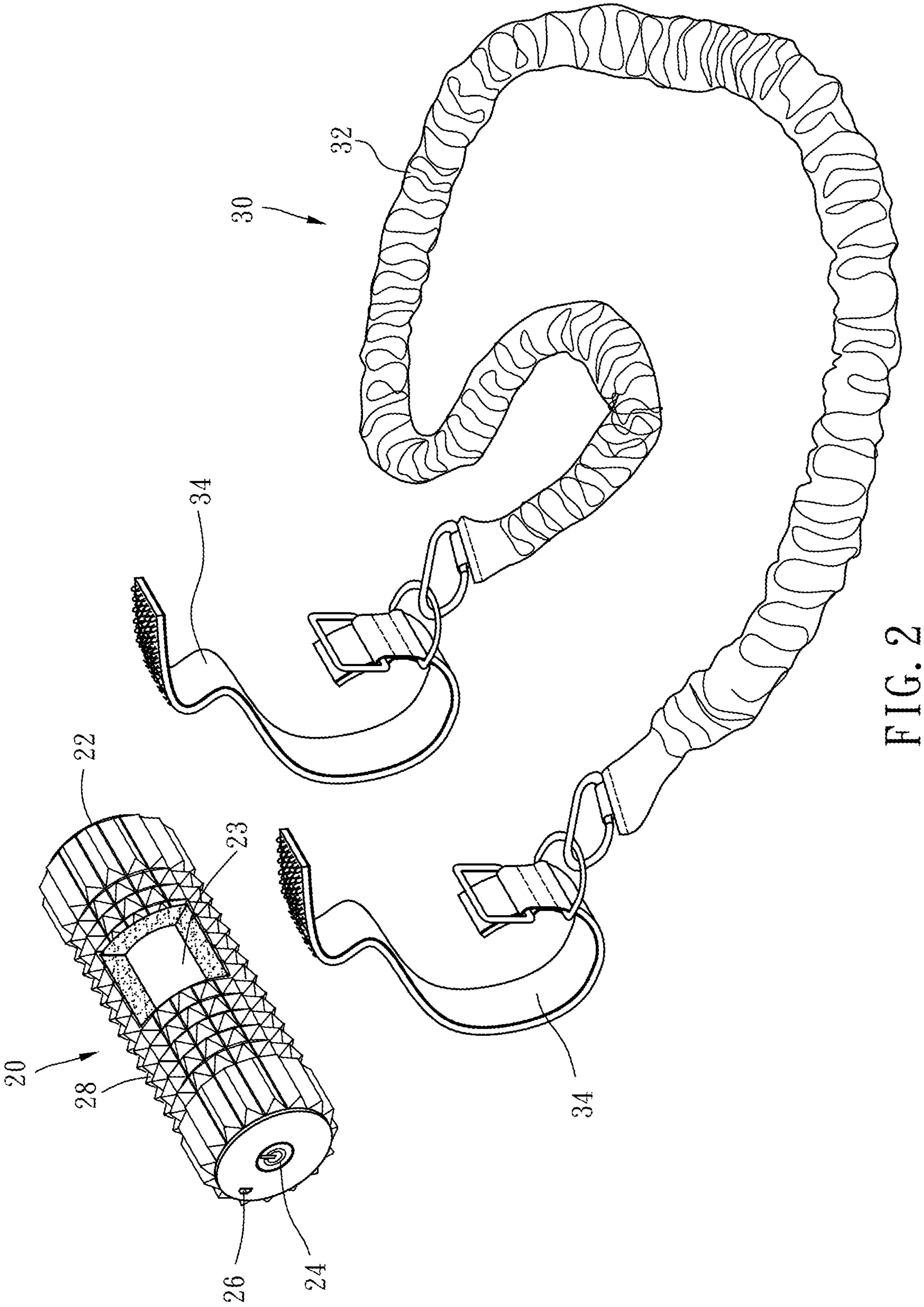
FIG. 2 is an exploded perspective view of the vibration elastic rope assembly according to the first preferred embodiment of the present invention.

Referring to FIGS. 1 and 2, a vibration elastic rope assembly 10 according to a first preferred embodiment of the present invention includes a vibrating unit 20 and an elastic unit 30.

The vibrating unit 20 has a shell 22 and a vibrator 23 disposed in the shell 22. In the present embodiment, the shell 22 has a cylindrical shape for conveniently being grasped and held within a user's hands; however, in other embodiment, the shell 22 may have a rectangular or irregular shape. The vibrating unit 20 has a touch switch 24 mounted at one end of the shell 22 and electrically connected to the vibrator 23 for turning the vibrator 23 on and off, and a charging port 26 mounted at one end of the shell 22 and electrically connected to the vibrator 23 for charging the vibrator 23. Further, the shell 22 has a plurality of flexible protrusions 28 at an outer surface thereof. When the user grasps the shell 22, the flexible protrusions 28 can be stopped against the user's palms to apply a massage effect. For the vibrator 23, various electricity-powered mechanical vibrating devices may be used. For example, an electric vibrator that is composed of an electric motor with an unbalanced mass on its driveshaft and commonly used in exercise apparatus may be used.

The elastic unit 30 has an elastic rope 32 and at least one connecting member 34. In the present embodiment, two connecting members 34 are provided. The two connecting members 34, which are annular belts, are sleeved on the shell 22 of the vibrating unit 20 and spaced apart at a predetermined distance. Preferably, the two connecting members 34 are sleeved on two ends of the shell 22 for allowing the user to grasp the shell 22 conveniently. In the present embodiment, the elastic rope 32 has two ends thereof connected to the two connecting members 34, respectively.

Figure 4:
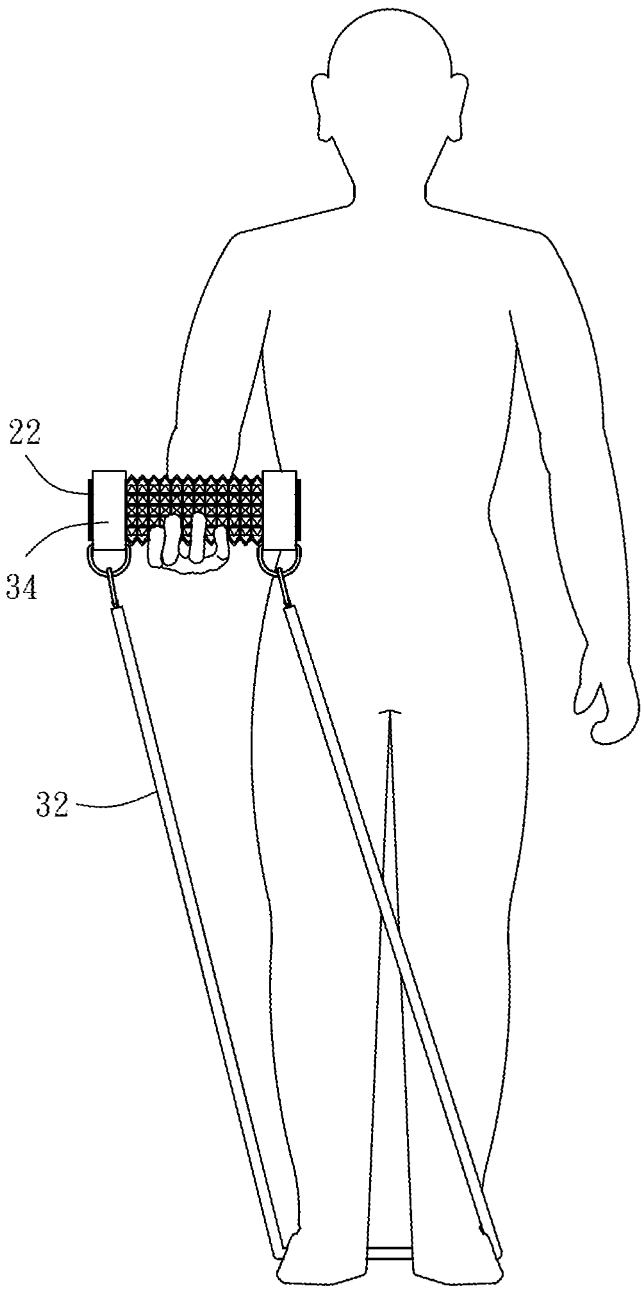
FIG. 4 is a schematic drawing of the vibration elastic rope assembly according to the first preferred embodiment of the present invention, showing the user steps on the middle of the elastic rope.

Referring to FIG. 4, when operating the vibration elastic rope assembly 10, the user can step on the middle of the elastic rope 32 and grasp the shell 22 by one or two hands, and then the user can lift and lower the shell 22 repeatedly to train the biceps muscles. Furthermore, the user can operate two different vibration elastic rope assemblies 10 at the same time to enhance training intensity and perform various types of exercises. For example, one of the vibration elastic rope assemblies 10 is operated by the left hand and foot, and the other one of the vibration elastic rope assemblies 10 is operated by the right hand and foot. Alternatively, one of the vibration elastic rope assemblies 10 is operated by the left hand and right foot, and the other one of the vibration elastic rope assemblies 10 is operated by the right hand and left foot.

Figure 3:
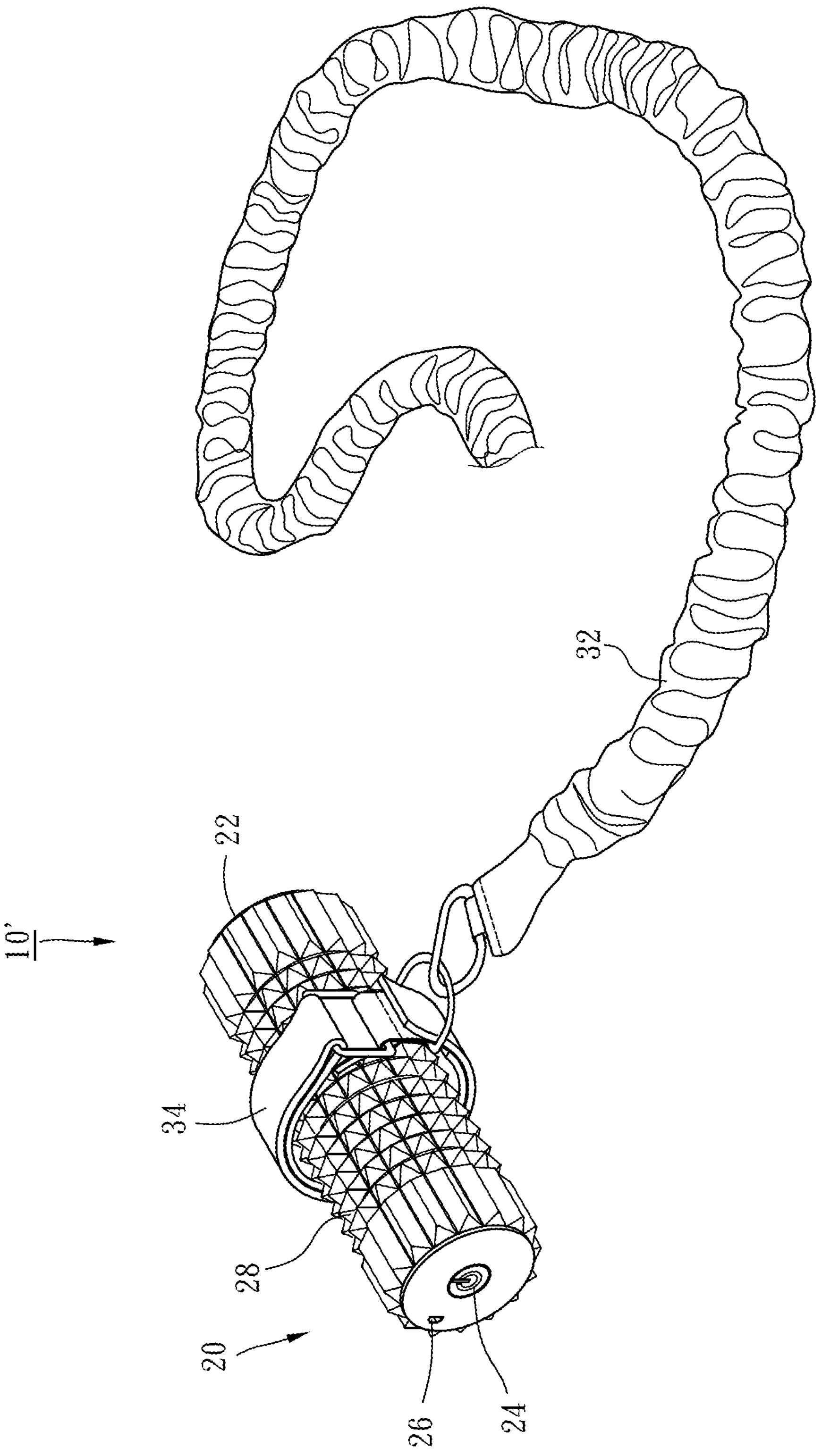
FIG. 3 is a perspective view of the vibration elastic rope assembly according to a second preferred embodiment of the present invention.

Referring to FIG. 3, in a second preferred embodiment of the vibration elastic rope assembly 10', only one connecting member 34 is provided. The connecting member 34 is an annular belt and sleeved on the shell 22. Preferably, the connecting member 34 is sleeved on the middle of the shell 22 for allowing the user to grasp the two ends of the shell 22 conveniently. In the second preferred embodiment, the elastic rope 32 has one end thereof connected to the connecting member 34 and the other end, which is a free end that can be detachably wrapped around or connected to the user's body, directly grasped by user's hand, or coupled to exercise equipment 40 (see FIG. 6).

Figure 5:
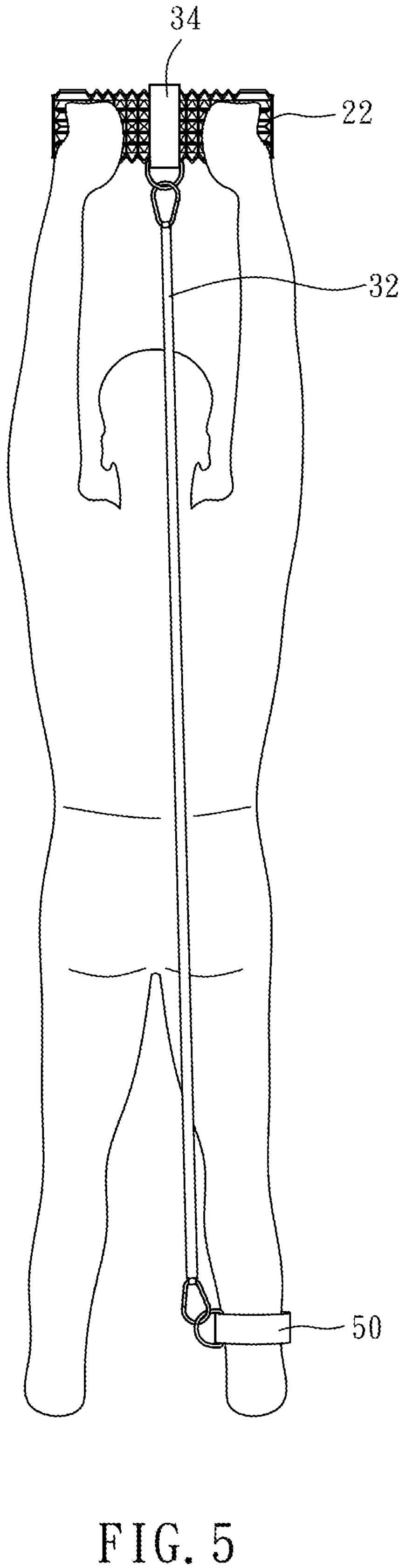
FIG. 5 is another schematic drawing of the vibration elastic rope assembly according to the second preferred embodiment of the present invention, showing one end of the elastic rope is sleeved on one of the user's feet.

Referring to FIG. 5, the user can grasp the two ends of the shell 22 by two hands in such a way that the elastic rope 32 is located behind the user and fastened to the user's lower calf through an annular member 50. As such, the user can raise both arms above shoulder to train the arm and back muscles.

Figure 6:
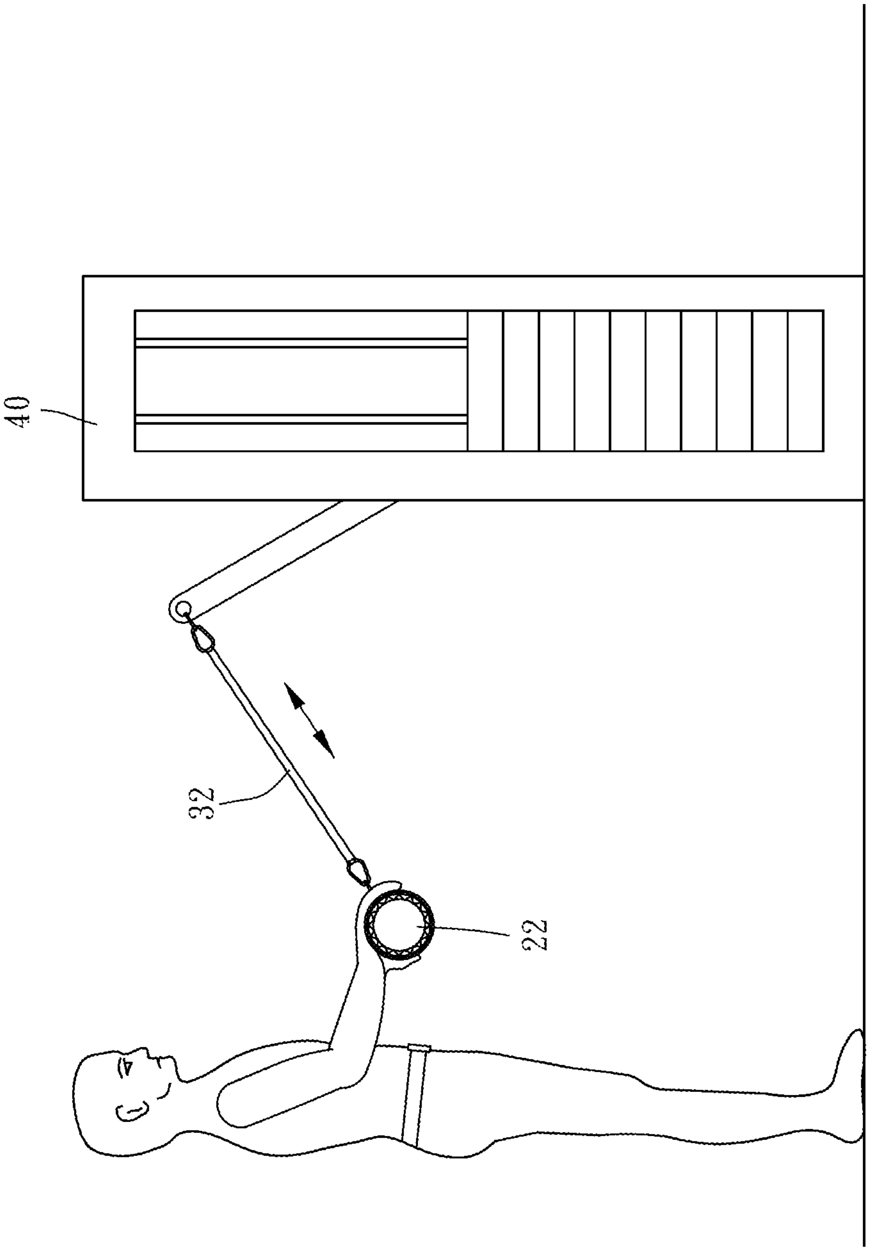
FIG. 6 is a schematic drawing of the vibration elastic rope assembly according to the second preferred embodiment of the present invention, showing one end of the elastic rope is fastened to the exercise equipment.

Referring to FIG. 6, one end of the elastic rope 32 is fastened to an exercise equipment 40, such that the user can pull and relax the elastic rope 32 repeatedly through the shell 22 to train the arm muscles.

In summary, the vibration elastic rope assembly 10, 10' can be operated in various ways to achieve the purposes of enhancing training intensity and performing different types of exercises. Further, by means of the flexible protrusions 28 of the shell 20 and the vibrator 23 installed in the shell 20, the massage effect can be applied to the user's palms and the vibration effect can be transmitted from the user's palms to the user's body, thereby improving the user's blood circulation.

What is claimed is:

1. A vibration elastic rope assembly comprising:

a vibrating unit having a cylindrical shell and a vibrator disposed in the cylindrical shell; and an elastic unit having at least one connecting member mounted on the cylindrical shell of the vibrating unit, and an elastic rope connected to said at least one connecting member;

whereby the elastic rope is configured to be detachably connected to a user's body or an exercise equipment for enabling the user to perform exercises;

wherein the elastic unit has two said connecting members, which are annular belts, sleeved on the cylindrical shell of the vibrating unit and connected to two ends of the elastic rope, respectively.

2. The vibration elastic rope assembly as claimed in claim 1, wherein the two connecting members are spaced apart at a predetermined distance.

3. The vibration elastic rope assembly as claimed in claim 1, wherein the cylindrical shell has a plurality of flexible protrusions at an outer surface thereof.

4. A vibration elastic rope assembly, comprising:

a vibrating unit having a cylindrical shell and a vibrator disposed in the cylindrical shell; and an elastic unit having at least one connecting member mounted on the cylindrical shell of the vibrating unit, and an elastic rope connected to said at least one connecting member;

whereby the elastic rope is configured to be detachably connected to a user's body or an exercise equipment for enabling the user to perform exercises;

wherein the elastic unit has one said connecting member, which is an annular belt and sleeved on the cylindrical shell of the vibrating unit; the elastic rope has one end thereof connected to the connecting member, and a free end.

5. The vibration elastic rope assembly as claimed in claim 4, wherein the cylindrical shell has a plurality of flexible protrusions at an outer surface thereof.

* * * * *